(12) United States Patent
Mickols et al.

(10) Patent No.: US 8,210,042 B2
(45) Date of Patent: Jul. 3, 2012

(54) USE OF ACOUSTIC SIGNALS FOR MEASURING MEMBRANE FOULING IN SPIRAL WOUND MODULES

(75) Inventors: William E. Mickols, Chanhassen, MN (US); Michael S. Koreltz, Bloomington, MN (US); David J. Moll, Midland, MI (US); Donald B. Streeter, Waconia, MN (US)

(73) Assignee: Dow Global Technologies LLC, Midland, MI (US)

( * ) Notice: Subject to any disclaimer, the term of this patent is extended or adjusted under 35 U.S.C. 154(b) by 924 days.

(21) Appl. No.: 11/709,528

(22) Filed: Feb. 22, 2007

(65) Prior Publication Data

US 2008/0202242 A1 Aug. 28, 2008

(51) Int. Cl.
*G01D 7/00* (2006.01)
*B01D 35/00* (2006.01)

(52) U.S. Cl. .......... 73/587; 73/579; 73/596; 73/597; 73/598; 73/599; 73/600; 73/614; 73/615; 73/616; 73/617; 73/618; 73/619; 73/620; 73/625; 73/626; 73/627; 73/628; 73/629; 210/85; 210/411; 210/650; 210/651; 210/785; 210/791

(58) Field of Classification Search .......... 210/85, 210/748, 785, 636, 321.69, 321.87; 73/587
See application file for complete search history.

(56) References Cited

U.S. PATENT DOCUMENTS

| | | | |
|---|---|---|---|
| 4,253,962 A | 3/1981 | Thompson | |
| 5,919,376 A | 7/1999 | Carmen | |
| 6,161,435 A | 12/2000 | Bond et al. | |
| 6,959,602 B2 | 11/2005 | Peterson, Jr. et al. | |
| 7,008,540 B1 | 3/2006 | Weavers et al. | |
| 2003/0217599 A1* | 11/2003 | Peterson et al. | 73/602 |
| 2005/0183739 A1 | 8/2005 | McDermott et al. | |

FOREIGN PATENT DOCUMENTS

DE 37 14 747 11/1988
(Continued)

OTHER PUBLICATIONS

Chai et al., "Ultrasound, Gravimetric, and SEM Studies of Inorganic Fouling in Spiral-Wound Membrane Modules", Desalination Jun. 18, 2006.

(Continued)

*Primary Examiner* — Krishnan S Menon
*Assistant Examiner* — Dirk Bass
(74) *Attorney, Agent, or Firm* — Edward W. Black

(57) ABSTRACT

A spiral wound module assembly comprising: a permeate collection tube, at least one membrane envelope wound about the permeate collection tube, an outer module housing, and at least one acoustic transducer located adjacent to the permeate collection tube. Several embodiments are disclosed including a stand-alone probe adapted for insertion into the permeate collection tube. In several other embodiments, one or more transducers are secured to the inner surface of the permeate collection tube. The invention further includes a method of measuring membrane fouling within a spiral wound module comprising the steps of: a) transmitting an acoustic signal from a location adjacent to the permeate collection tube; b) receiving an echo signal resulting from the transmitted acoustic signal reflecting from an interface within the module; c) providing a reference signal corresponding to a known state of membrane fouling; d) comparing the echo signal to the reference signal; and e) determining a state of membrane fouling based upon the comparison of the echo signal and reference signal.

7 Claims, 7 Drawing Sheets

FOREIGN PATENT DOCUMENTS

FR        2 552 652        4/1985

OTHER PUBLICATIONS

Zhang, et al., "Study of Membrane Fouling and Cleaning in Spiral Wound Modules Using Ultrasonic Time-Domain Reflectometry", New Insights into Membrane Science and Technology: Polymeric, Inorganic and Biofunctional Membranes.

Chai et al., "In Situ Ultrasonic Measurement of Fouling and Cleaning Processes in Spiral-Wound Membrane Modules", Membrane Technology in Water and Wastewater Treatment, pp. 266-267, Royal Society of Chemistry.

Deutsch V et al, Ultraschallpruefung: Grundlagen Und Industrielle Anwendungen, pp. 41, 42, 215, 216, XP002491472.

* cited by examiner

Acoustic Signal (milli-Volts) vs. Time (micro-Seconds)

Amplitude (Volts) vs. Frequency (Mega Hertz) for Region A

Percent Feed Flow Loss & Normalized Amplitude Sum vs. Hours of Operation

USE OF ACOUSTIC SIGNALS FOR MEASURING MEMBRANE FOULING IN SPIRAL WOUND MODULES

BACKGROUND OF THE INVENTION (1) Field of the Invention

The invention includes an apparatus and method of using acoustic waves ("signals") to measure membrane fouling within a spiral wound membrane module. In one preferred embodiment, the invention includes a spiral wound module assembly including at least one membrane envelope wound about a permeate collection tube, an outer module housing, and an acoustic transducer located adjacent to the permeate collection tube. Acoustic signals are transmitted and received by the transducer and are compared with a reference signal to determine the state of membrane fouling.

(2) Description of the Related Art

Membrane fouling is a common problem in most membrane based separation processes. Membrane fouling is a chemical phenomenon where solutes are deposited upon the membrane surface resulting in reduced membrane flux and selectivity. Failure to timely clean membranes can result in higher cleaning costs (e.g. longer cleaning times, additional cleaning agents, use of more aggressive cleaning agents, etc.) and premature module replacement. Loss of operating time and increased costs associated with membrane cleaning and premature module replacement along with reduced operating performance result in overall increased separation costs. Thus, it is important to carefully monitor membrane fouling in order to optimize module performance, cleaning and longevity.

Spiral wound module configurations present specific challenges with respect to membrane fouling. Due to their spiral configuration, it is difficult to visually inspect the membrane surface without destroying or otherwise compromising the integrity of the module. Thus, membrane fouling is commonly monitored by a variety of indirect measures including: permeate flow rates, permeate recovery ratios, operating pressures, feed temperatures and permeate quality. Unfortunately, these indirect measures can be influenced by factors unrelated to membrane fouling, such as concentration polarization.

U.S. Pat. No. 6,161,435 describes a non-destructive, in-situ, real time, direct method for monitoring membrane fouling of spiral wound membrane module using Acoustic Time-Domain Reflectometry (ATDR), also referred to as UTDR (Ultrasonic Time-Domain Reflectometry). The module assembly includes acoustic piezoelectric transducers located on the outer housing of the module. Acoustic pulse signals are transmitted inward through the housing and into the spirally wound membrane envelopes. When the signal pulses encounter an interface, such as one formed between the feed solution and the top surface of the membrane envelope, a portion of the signal is reflected back to the transducer as an echo signal. The amplitude of the reflected signals depends on the acoustic impedance difference between the media or either side of the interface and the topography of the interface. The acoustic impedance is a function of the physical characteristics of the medium and is defined by the product of the density and acoustic signal velocity through the medium. Since the impedance, interface properties and path length change with an increase of fouling on the membrane surface, the change in amplitude, phase and the shift in arrival time of the interface echoes can be analyzed and used to monitor membrane fouling in real-time. Echo signals are compared via a signal processor with a reference signal (corresponding to an earlier measurement or a measurement from a database corresponding to a non-fouled membrane) so that the relative state of fouling or cleaning can be directly measured in real time.

Further descriptions of ultrasonic techniques for monitoring membrane fouling of spiral wound modules are provided in: Chai, G. Y., Greenberg, A. R., and Krantz W. B, *In-situ Ultrasonic Measurements of Fouling and Cleaning Processes in Spiral-Wound Membrane Modules*, Membrane Technology in Water and Wastewater Treatment 249, 266-257, (2000) Royal Society of Chemistry; Chai, G. Y., Greenberg, A. R., and Krantz W. B., *Ultrasound, Gravimetric and SEM Studies of Inorganic Fouling in Spiral Wound Membrane Modules*, Desalination 208, 277-293 (2007), Elsevier, Amsterdam; and Zhang, Zh.-X, Greenberg, A. R., Krantz, W. B.; and Chai, G. Y., *Study of Membrane Fouling and Cleaning in Spiral Wound Modules Using Ultrasonic Time-Domain Reflectometry*, New Insights into Membrane Science and Technology: Polymeric and Biofunctional Membranes, 65-88, (2003), A. A. Butterfield and D. Bhattacharyya, eds. Elsevier, Amsterdam. This latter reference indicates that the application of ultrasound to spiral wound modules is complicated by several factors including a much more complex signal pattern resulting from multiple reflections from the surface layers of multiple layers within spiral wound modules and loss of acoustic information caused by signal attenuation through these multiple layers as well as through the module housing. The reference goes on to describe a signal acquisition and analysis protocol which attempts to account for systematic shifts in the entire acoustic spectrum as a function of module operating time and enables information about the state of fouling to be obtained in real-time.

The outer housings of many commercially available spiral wound modules are made from fiber reinforced plastic, (e.g. glass fiber wrapped about wound membrane envelopes, coated or impregnated with a thermoplastic or thermoset resin such as an epoxy material). Unlike the relatively homogenous housing materials utilized with some modules, (e.g. stainless steel and polyvinylchloride), fiber reinforced plastics tend to scatter acoustic signals. That is, the combination of materials having distinct acoustic impedance properties along with many internal interfaces within an integral composite structure makes the interpretation of acoustic signals exceedingly difficult. As a consequence, the use of acoustic measurements through the outer housing of many spiral wound modules is quite limited. Moreover, unlike the aforementioned publications which focus on relatively small modules (e.g. 2.5 inch diameter), most industrial modules are much larger (e.g. 8 inch diameter and even larger). Due to their weight and dimension, these larger modules include much thicker outer housings. The use of relatively thicker fiber reinforced plastic housings further minimizes the utility of the aforementioned ultrasonic techniques.

Membrane fouling tends to initiate and be most pronounced in areas experiencing the highest permeate flux, i.e. areas of the membrane envelope adjacent to the permeate collection tube. Due to their spiral wound configuration, these susceptible areas of the membrane are wrapped within many concentric layers. That is, the most critical area of membrane surface for determining fouling is located at the most distant location from the outer housing of the module and is insulated by many concentric layers (e.g. membrane envelops, feed spacers, permeate spacers, etc.). Due to limitations of acoustic signal strength and the ever increasing complexity of interpreting reflective signals from multiple interfaces, the aforementioned ultrasound techniques are limited to examining only the outermost membrane layers. Unfortunately, these outer layers typically include tape and excess permeate and feed spacers as well as glued sections of membrane which are attached to the permeate spacer. Thus, the outer layers provide a less instructive measure of membrane fouling. That is, in order to take timely corrective action (e.g. cleaning, modification of feed quality, etc.), a measure of membrane fouling in the areas where fouling is initiated and/or most pronounced is desired.

In addition to monitoring membrane fouling, ultrasound has been described in a variety of other membrane applications including detecting membrane defects (U.S. Pat. No. 6,959,602), and membrane cleaning (U.S. Pat. Nos. 5,919, 376 and 7,008,540)—including membrane cleaning from within spiral wound modules (U.S. Pat. No. 4,253,962).

BRIEF SUMMARY OF THE INVENTION

The present invention includes several embodiments for measuring membrane fouling within a spiral wound module. In one preferred embodiment, the invention includes a spiral wound module assembly comprising: a permeate collection tube, at least on membrane envelope wound about the permeate collection tube, an outer module housing, and at least one acoustic transducer located adjacent to the permeate collection tube. The invention further includes a stand-alone probe adapted for removable insertion into a permeate collection tube of a spiral wound module. The invention also includes a method of measuring membrane fouling within a spiral wound module comprising the steps of: a) transmitting an acoustic signal from a location adjacent to the permeate collection tube; b) receiving an echo signal resulting from the transmitted acoustic signal reflecting from an interface within the module; c) providing a reference signal corresponding to a known state of membrane fouling; d) comparing the echo signal to the reference signal; and e) determining a state of membrane fouling based upon the comparison of the echo signal and the reference signal.

The present invention overcomes one or more of the aforementioned deficiencies of the prior art by locating an acoustic transducer adjacent to the permeate collection tube. Preferred embodiments of the present invention allow for early detection of membrane fouling and/or the measurement of fouling of membrane surfaces adjacent to the permeate collection tube. Moreover, preferred embodiments of the invention are broadly applicable to spiral wound modules including those of large diameter (i.e. many concentric layers) and/or those having fiber reinforced plastic outer housings. Preferred embodiments of the invention are well suited for in-situ, on-line, real-time measurements during standard module operation and/or cleaning, or while the module is off-line. Thus, module performance, maintenance, replacement, and/or cleaning can be optimized based upon a direct measurement of membrane fouling. Many additional embodiments, objectives, advantages and features are disclosed.

DETAILED DESCRIPTION OF THE INVENTION

Figure 1:
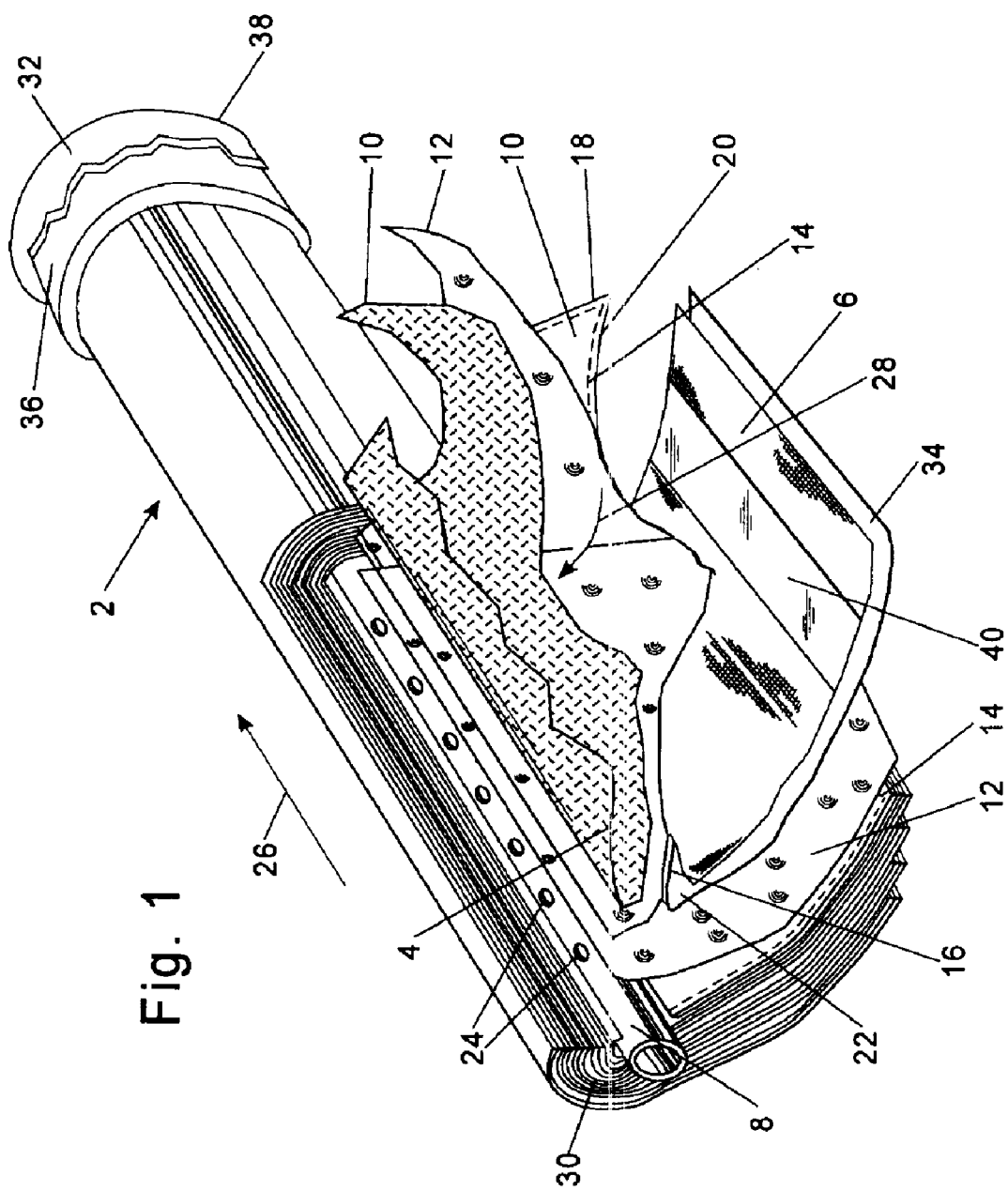
FIG. 1 is a perspective, partially cut-away view of a spiral wound module.

The invention includes a spiral wound module assembly. The phrase "spiral wound module assembly" is intended to describe a spiral wound module along with one or more additional components associated with acoustic measurement, including but not limited to: an acoustic transducer, signal processor, communication means, and/or acoustic reference member. The spiral wound module of the present invention is not particularly limited and many different configurations and sizes are applicable to the invention. Such modules have been used in a variety of fluid separations for over thirty years including both gas and liquid phase separations. Due to their spiral configuration, a relatively large membrane surface area can be packed into an individual module. Depending upon the specific membrane used, spiral wound modules can be used in a wide variety of applications including: reverse osmosis (RO), nanofiltration (NF), ultrafiltration (UF) and microfiltration (MF). Examples of common aqueous-based liquid separations utilizing spiral wound modules include the treatment of feeds such as the concentration and/or salt removal in food, dairy and sweetener feeds; desalination of water, removal divalent ionic species such as calcium and barium ions, and removal of larger constituents such as cysts, viruses, and pesticides. A typical module includes a permeate collection tube, at least one but preferably many membrane envelopes, and an outer housing. The outer housing comprises an outer shell and is typically cylindrical in shape and may be constructed from a variety of materials; however, fiber reinforced plastics (e.g. epoxy resin reinforced with glass fibers), stainless steel, PVC, and tape are most common. For many applications, fiber reinforced plastic materials are particularly preferred.

The type of membrane and number of membrane envelopes is not particularly limited. The selection of membrane is dependant upon the specific application, feed source, solute, and foulants. RO and NF membranes have traditionally been made from cellulose acetate materials or a composite material comprising a microporous sheet and a thin film "discriminating layer". One example is FilmTec Corporation's FT'30™ membrane which comprises a microporous polysulfone sheet with a thin film polyamide layer. The polyamide layer is obtained by an interfacial polycondensation reaction between a polyfunctional amine monomer and a polyfunctional acyl halide monomer as described in U.S. Pat. Nos. 4,277,344 to Cadotte and 6,878,278 to Mickols. Methods of improving membrane performance by post-treatment are described in U.S. Pat. Nos. 5,876,602 to Jons et. al., 5,755,964 to Mickols and 4,765,897 to Cadotte. Methods for reducing membrane fouling by chemical modification of the membrane surface are described in U.S. Pat. No. 6,280,853 to Mickols. While modules are available in a variety of sizes, one of the more common industrial RO modules is available with a standard 8 inch diameter and 40 inch length (8×40). For a typical 8 inch diameter module, 26 to 30 individual membrane envelopes are wound around the permeate collection tube. In operation, five to eight modules are often serially connected within a common pressure vessel. Examples of commercially available spiral wound modules include the following products available from FilmTec Corporation: BW30-XLE-400 brackish water module, SW30-XLE-400i sea water desalination module, and NF-400 nanofiltration module.

A spiral wound module assembly suitable for use in the present invention is generally shown at (2) in FIG. 1. The module (2) is formed by wrapping one or more membrane leaves or "envelopes" (4) and optional feed channel spacer sheet(s) ("feed spacers") (6) about a permeate collection tube (8). The membrane envelopes (4) comprise two substantially rectangular membrane sheets (10) surrounding a permeate channel spacer sheet ("permeate spacer") (12). This sandwich-type structure is secured together, e.g. by adhesive (14), along three edges (16, 18, 20) while the fourth edge (22) abuts the permeate collection tube (8) so that the permeate spacer (12) is in fluid contact with openings (24) passing through the permeate collection tube (8). Each envelope (4) is preferably separated by a feed spacer (6) that is also wound about the collection tube (8). While not shown, additional intermediate layers may also be included in the assembly.

Arrows shown in FIG. 1 represent the approximate flow directions (26, 28) of feed and permeate during operation. Feed flow (26) is from the inlet end (30) to the outlet (sometimes also referred to as "concentrate") end (32) across the front surface (34) of the membrane. Permeate flow (28) is along the permeate spacer (12) in a direction approximately perpendicular to the feed flow (26). Actual flow paths vary with details of construction and operating conditions. During module fabrication, the membrane envelope(s) (4) and feed spacer(s) (6) are wound about the permeate collection tube and then held in place such as by tape (e.g. self adhering mesh tape) until an outer housing (36) can be secured about the partially constructed module (2). While stainless steel, tape and PVC materials are used in some applications, one of the most common module housing materials is made from fiber reinforced plastics, e.g. long glass fibers coated with a thermoplastic or thermoset resin. During module fabrication, long glass fibers are wound about the partially constructed module and resin (e.g. liquid epoxy) is applied and hardened. The fiber glass outer housing (36) provides a protective yet inexpensive outer shell. The end of modules are often fitted with an anti-telescoping device or end cap (38) designed to prevent membrane envelops from shifting under the pressure differential between the inlet (30) and outlet (32) ends of the module. The end cap (38) is commonly fitted with an elastomeric seal (not shown) to form a tight fluid connection between the module and an external pressure vessel (not shown). As will be described in more detail, several embodiments of the present invention further include an acoustic reference member (40) which may comprise a strip or layer of metal foil or other acoustically differentiated material, i.e. a material that possess an acoustic impedance that is significantly different than adjacent materials.

The construction of spiral wound modules is further described in U.S. Pat. Nos. 5,538,642 to Solie and 5,681,467 to Hallan et. al. Feed spacers are described in more detail in U.S. Pat. No. 6,881,336 to Johnson. Several preferred end cap designs are described in U.S. Pat. No. 6,632,356 to Hallan, et al., including FilmTec Corporation's iLEC™ interlocking end caps. WO 2006/026011 to ions et. al. describes methods for detecting defects in spiral wound modules including specific embodiments direct toward the use of conductivity cells positioned within the permeate collection tube to measure permeate conductivity.

Figure 2A:
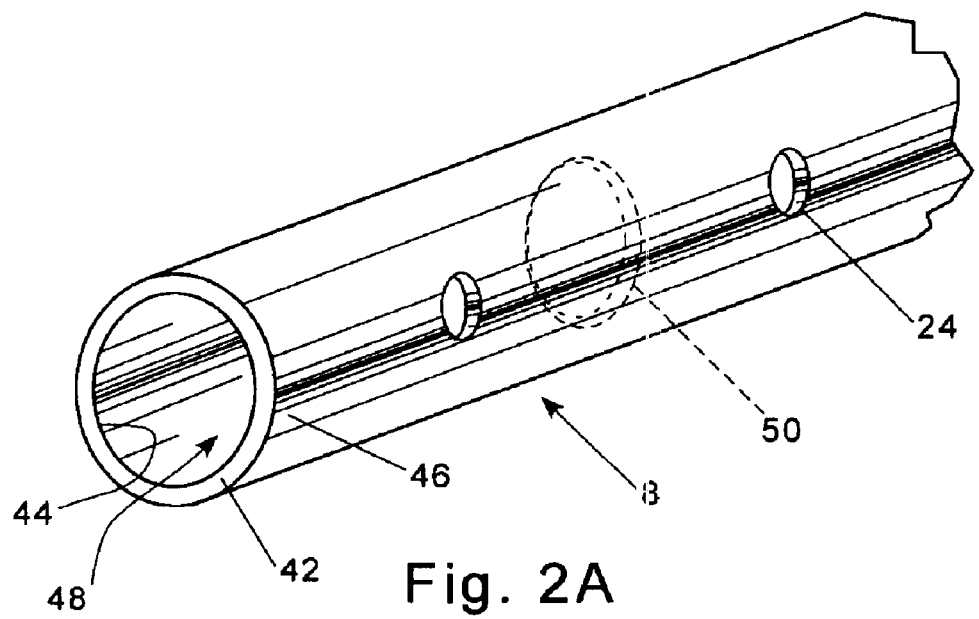
FIG. 2*a* is perspective, partially cut-away view of one embodiment of a permeate collection tube.

FIG. 2a is a perspective, partially cut-away view of a permeate collection tube, generally shown at (8). The tube (8) comprises a cylindrical wall (42) including an inner (44) and outer surface (46), and an inner space (48) defined by the surrounding inner surface (44) of the cylindrical wall (42). The tube (8) includes openings (24) for receiving permeate into the inner space (48) of the tube (8). In one embodiment of the invention, the permeate collection tube (8) further includes a transmission window (50) extending through at least a portion of the cylindrical wall (42). The transmission window (50) is an area of the cylindrical wall (42) comprising a material having a different acoustic impedance than the material ("first material") comprising the majority or "bulk" of the tube (8). In a preferred embodiment, the transmission window (50) comprises a material ("second material") having an acoustic impedance closer to that of water as compared to the material comprising the bulk of the tube (8). Use of a transmission window (50) permits a broader range of materials to be used in the construction of the bulk of the tube (8). As will become clear from a review of the entire specification, an acoustic transmitter (not shown) may be located within the permeate collection tube (8) and directly adjacent to the transmission window (50). In this way, the remainder of the tube (8) may be constructed from materials that scatter or adsorb acoustic signals without negatively effecting the present invention. Thus, the permeate collection tube (8) may be made from a wide variety of materials. For purposes of other preferred embodiments, the permeate collection tube (8) does not include a transmission window and the entire tube is made from a material that permits effective transmission and receipt of acoustic signal. Examples of suitable materials include plastic materials as: polyethylene, polypropylene, polystyrene, polyvinyl chloride, polysulfone, poly (phenylene oxide), acrylonitrile-butadiene-styrene (ABS), but ABS and polysulfone are particularly preferred. While not required, materials having acoustic impedance properties similar to water are also preferred.

The spiral wound module assembly includes one or more (e.g. one to six) acoustic transducers located at a variety of locations within the module and adjacent to the permeate collection tube. Several specific embodiments are described. The term "acoustic transducer" is intended to mean a device for sending and receiving acoustic signals. For purposes of the invention, it is preferred that the transducer include both an acoustic signal transmitter and receiver within a single unit or device; however, it will be understood that these units may be separate. In those embodiments where the transmitter and receiver are separate units, both are included and both are located adjacent to the permeate collection tube. While the type of transducer is not particularly limited, its size and shape will often be dictated by the dimensions of the module, and particular the permeate collection tube. As will be described in more detail, a preferred transducer is capable of operating within frequency range from about 0.5 to 20 MHz, preferably 1 to 3 MHz, with an energy from about 10 to 200 µJ, preferably 50 to 150 µJ, and a pulse rate of from 0.1 MHz to 500 KHz.

As mentioned, the transducers are located adjacent to the permeate collection tube. The phrase "adjacent to" means: 1) within the permeate collection tube including: i) within the inner space defined by the inner surface of the permeate collection tube, ii) on the inner surface of the permeate collection tube, and iii) within (e.g. molded or embedded into) the cylindrical wall of the permeate collection tube; 2) extending through the cylindrical wall of the tube; and 3) on or near the outer surface of the permeate collection tube. In order to reduce signal noise and other undesired signals, the transducer is preferably secured to the permeate collection tube in a manner to restriction relative movement between the transducer and tube. The term "secured" is intended to include both: 1) a permeate connection, (e.g. wherein the transducer is integrally molded into the tube, sonically welded to a surface of the tube, adhered to a surface of the tube with a irreversible bonding agent, etc.) and 2) a temporary or reversible connection where the transducer may be subsequently removed from the permeate collection tube after testing, or where the transducer may be moved to multiple locations adjacent to the tube. Non-limiting examples of such temporary connections include: a weak or reversible adhesive bond, a removable contact pad that allows acoustic coupling between the transducer and the inner surface of the permeate collection tube, a removable probe which is adapted to be inserted into the inner space of the tube, a mechanical interlocking mechanisms such as regress within the inner surface of the tube having a shape for receiving a transducer, an interlocking slidable groove/slot connector between the outer housing of the transducer and a surface of the tube, and/or providing the transducer as part of a cylindrical sleeve having and outer diameter slightly smaller than the inner diameter of the tube such that the sleeve can be removably inserted into the tube. This list of embodiments is only intended to be representative of many applicable embodiments. For many applications, the shape and size of readily available transducers may dictate the final embodiment for securing the transducer to the tube. In general, if the transducer is located within the tube, the size and shape of the transducer should be such as to not unduly restrict flow of permeate into or through the tube. When utilizing relatively small permeate collection tubes such as those provided with 2.5 inch diameter modules, minimization of the transducer may be necessary.

Figure 2B:
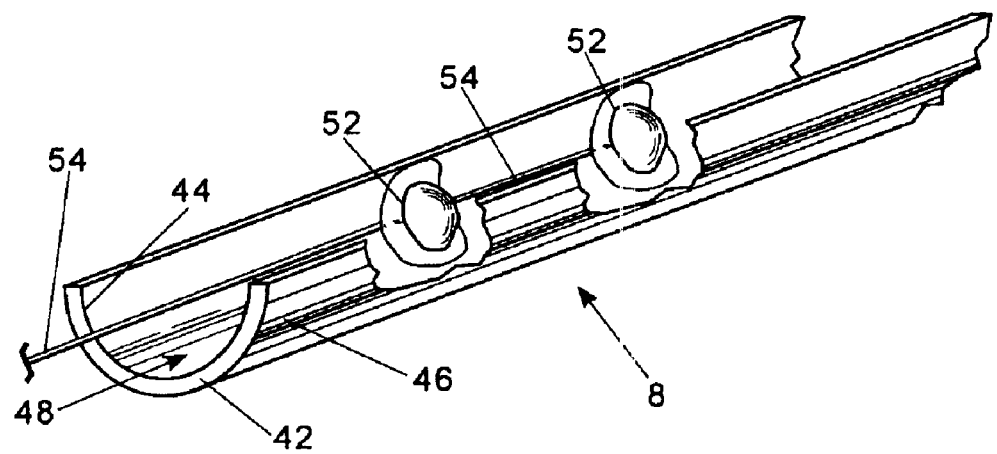
FIG. 2*b* is a perspective, partially cut-away view of another embodiment of permeate collection tube.

One preferred embodiment of a permeate collection tube is shown in FIG. 2b, wherein common features with the embodiment of FIG. 2a have been designated with common reference numerals. The permeate collection tube is generally shown at (8). The tube (8) comprises a cylindrical wall (42) including an inner (44) and outer surface (46), and an inner space (48) defined by the surrounding inner surface (44) of the cylindrical wall (42). The embodiment includes multiple acoustic transducers (52) secured to the inner surface (44) of the tube (8), such as by way of adhesive. The transmitting/receiving surface (not shown) of the transducer (52) is facing the inner surface (44) of the tube (8). As is common in acoustic applications, the interface between the transducer (52) and the inner surface (44) of the tube (8) may be coated with a viscous fluid or film designed to modify the acoustic impedance at the interface. Preferably the surface of the transducer (52) in contact with the inner surface (44) of the tube (8) has a matching or corresponding shape (i.e. radius of curvature) in order to make a close, concentric interface. The transducers (52) may be interconnected by a communication means, such as a conducting wire (54) for transmitting power and/or signals from a signal processor (not shown). The wire (54) is shown extending out from one of end of the tube (8). While not shown, in an alternative embodiment the communications means, e.g. wire, fiber optical conduit, metal strip, or equivalent communicating member may be molded into or embedded into the cylindrical wall (42) of the tube (8). In such embodiments, the end of the tube (8) may be fitted with a conductive member for communication with a power and/Dr signal processor. Alternatively, the communication means may comprise a wireless connection (e.g. a wireless local area network—WLAN) for communicating with the transducers. Such wireless communication means include known devices and equipment including by example: radio, WiFi and WiMAX communication devices.

While not shown, the inner surface of the cylindrical wall of the tube may include grooves, ridges or similar structures that engage with the outside of the transducer and permit the transmitter to be slidably secured to the inner surface such that a transducer may be relocated within the tube in order to take measurements at multiple locations.

Figure 3:
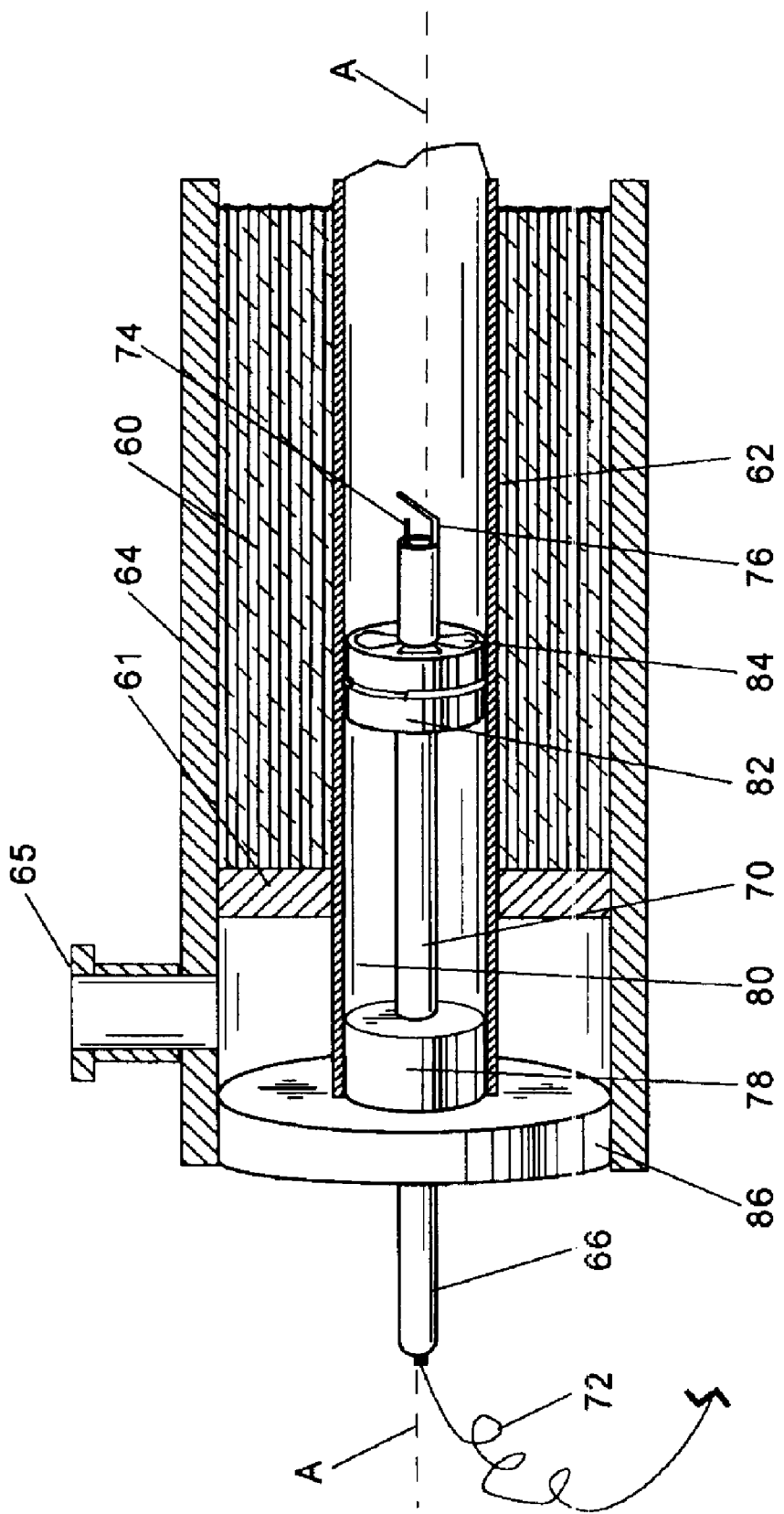
FIG. 3 is a cross-sectional, perspective view of a spiral wound module located within a pressure vessel shown including a removable probe positioned within the permeate collection tube.

In yet another embodiment, the transducer is provided as part of a probe adapted to be removably inserted into the end of a permeate collection tuba. For example, FIG. 3 shows a cross-sectional view (not to scale) of a spiral wound module (60) including an end cap (61) and permeate collection tube (62) located within a pressure vessel (64) including a side feed inlet (65). A probe (66) is shown inserted into the end of a permeate collection the (62) of the module (60). The probe (66) comprises a cylindrical body (70) including a wire (72) connected to a proximate end of the probe and an acoustic transducer (74) located at a distal end. An acoustic reflector (76) is positioned adjacent to the acoustic transducer (74) and is adapted to direct acoustic signals in a direction perpendicular to an axis (A) defined by the permeate collection tube (62). The acoustic reflector (76) may be made from any suitable material capable of reflecting acoustic signals but is preferably a highly polished metal surface. While not shown, the wire (72) or other communication means (e.g. fiber optic conduit, wireless connector, etc.) may be connected to a power and/or signal processor such as a computer controlled ultrasonic pulser/receiver. The probe (66) further includes a base (78) concentrically disposed about a portion of the body (70). The base (78) has an outer dimension corresponding (e.g. slightly smaller) than the inner surface (80) of the cylindrical wall of the permeate collection tube (62) such that the base (78) slidably engages the inner surface (80) of the cylindrical wall of the tube (62). That is, when inserted into the end of the tube (62), the base (78) forms a pressure fit with the inner surface (80) of the tube (62). While shown cylindrical, the base (78) may have alternative outer shapes, e.g. hexagonal, X-shaped, etc. Depending upon the arrangement of the module (60) within the pressure vessel (64) and the direction of feed flow, the base (78) may include one or more apertures for permitting fluid flow through the base (78). Alternatively, the base (78) may form an effective seal for preventing fluid flow into the permeate collection tube (62). The probe (66) is shown with an optional secondary base (82) located mar the distal end of the probe, adjacent to the transducer (74). The outer circumference of the secondary base (82) slidably engages the inner surface (80) of the tube (68) in order to restrict movement or the probe (66) relative to the tube (68). As with the base (78), the secondary base (82) may have alternative outer configurations, e.g. hexagonal, X-shaped, etc. The secondary base (82) is shown with apertures (84) for permitting permeate flow through the tube (62). The pressure fit of the bases (78, 82) ensures that the probe (66) remains relatively stationary, thereby permitting reproducible acoustic measurements to be obtained. While shown with two bases (78, 82), those skilled in the art will appreciate a wide variety of alternative embodiments. The probe (66) is shown disposed through an end plate (86) which seals the end of the pressure vessel (64). The end plate (86) has an outer diameter slightly smaller than the inner diameter of the pressure vessel (64) and is designed to perfect a fluid seal when secured in place. In an alternative embodiment, the probe (66) may be secured to the end plate (86) to form an integral unit.

Figure 4:
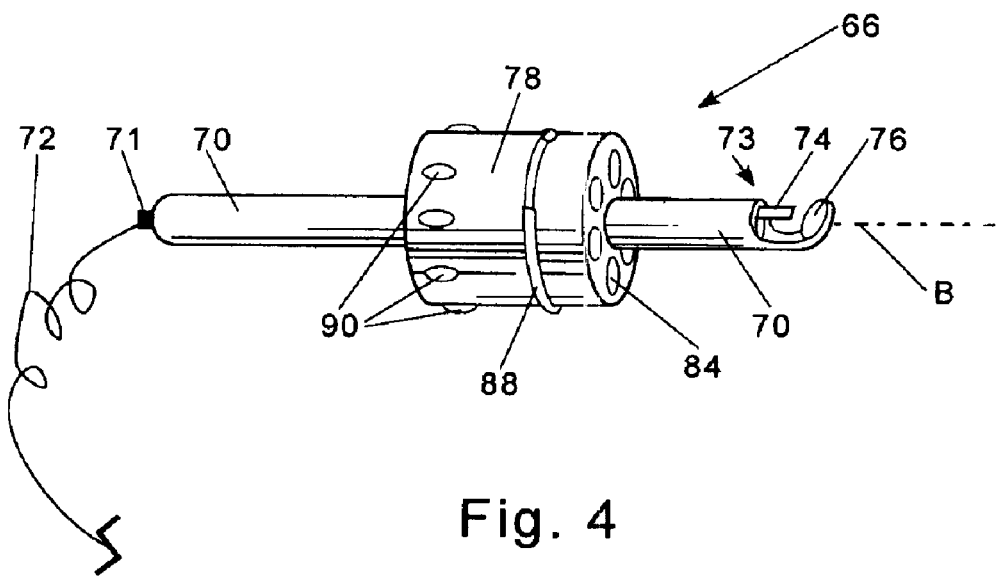
FIG. 4 is a perspective view of a stand-alone probe include an acoustic transducer located at a distal end.

The invention further includes a stand-alone, specially adapted probe as previously described with reference to FIG. 3, and as further described in an alternative embodiment shown in FIG. 4 wherein common features have been designated with common reference numerals. The probe is generally shown (not to scale) at (66) comprising an elongated body (70) extending along an axis (B) between a proximate (71) and distal end (73). The probe includes a base (78) concentrically disposed about a portion of the body (70). The base (78) includes an outer dimension corresponding to the inner surface of a permeate collection tube such that the base (78) is capable of slidably engaging an inner surface of a permeate collection tube. While shown cylindrical, the base (78) may have alternative outer shapes, e.g. hexagonal, X-shaped, etc. The probe includes at least one acoustic transducer (74) located at the distal end (73) of said probe (66), (such as Model A306S-SU immersion 2.25 MHz transducer available from Panametrics. The probe additionally includes an optional acoustic reflector (76) positioned adjacent to the transducer (74) in an orientation to direct acoustic signals to and from the transducer (74) in a direction substantially perpendicular to axis B defined by the body (70). In an alternative embodiment not shown, the transducer may be located in a manner to transmit and receive signals in a direction substantially perpendicular to axis B, in which case the acoustic reflector is unnecessary. The probe (66) further includes a communication means, such as a wire or fiber optic conduit (72) located at the proximate end (71) of the probe (66) for transmitting power and/or signals from a signal processor (not shown) to the transducer (74). The base (78) may further include one or more apertures or channels (84) running axially through the base (78) for permitting fluid flow through the base (78). The base (78) may also include one or more engagement members (88, 90) extending from the outer surface of the base for engaging the inner surface of a permeate collection tube (not shown). Preferably, the engagement member (88, 90) permits the probe to be axially slide into and out of a permeate collection tube (not shown), while simultaneously preventing non-axial movement between the probe and tube, particularly during membrane fouling measurement. The engagement member (88, 90) may comprise a variety of embodiments, including a raised concentric ring (88) including a smooth raised surface to facilitate contact and sliding action with the inner surface of the permeate collection tube. Alternatively, the engagement member may comprise a series of individual raised protrusions (90). The engagement member (88, 90) may comprise an elastomeric or foam-type material which is flexible and can ensure secure contact with the inner surfaces of permeate collection tubes which having slightly different internal diameters. Alternatively, the engagement member may comprise a lubricious material, e.g. polytetrafluoroethylene, for facilitating sliding engagement with the inner surface of a permeate collection tube.

The invention further includes a method of measuring membrane fouling within a spiral wound module by utilizing acoustic signals. The term "measuring" is intended to encompass both detection and monitoring. In its simplest terms, "measuring" is intended to mean: the acquisition of one value (data point) from the membrane and its comparison to a reference value. The reference value may be derived from the same membrane (e.g. acquired in an earlier state) or from another source such as a database of values corresponding to similar membranes in known states. The difference between the measured value and the reference value forms the basis for the determination of the state of fouling. In such a simplified example, a one time comparison can be described as the "detection" of fouling (or lack thereof), whereas a series of such comparisons permits "monitoring" of the state of fouling. Monitoring also permits more accurate predictions of future fouling. The phrases "state of fouling" or "state of membrane fouling" are not intended to be limited to a particular degree of fouling, source of fouling, or a process of fouling and/or cleaning. Rather, the phases are merely intended to refer to a relative comparison between at least two membrane-related fouling values. The phrase "membrane fouling" refers to the accumulation of debris on, in or near the surface of a membrane which results in reduced permeate flow. The types of debris or "foulants" depend greatly upon the source of the feed liquid. For aqueous feeds, foul ants can typically be classified into four general groups: scale—caused by precipitation of dissolved metal salts such as calcium carbonate, calcium sulfate and barium sulfate; silt—formed by suspended particulates such as colloidal silica, organic colloids, iron corrosion, and algae; biofouling—caused by the growth of microorganisms; and organic—such as grease, oil and surfactants.

A general description of relevant theory, equipment and methodologies for using acoustics to measure membrane fouling is provided in the references described in the Background Section, including U.S. Pat. No. 6,161,435 which is incorporated herein in its entirety by reference. However, it should be appreciated that the present invention includes applications of acoustics extending beyond those described in the previously described references. More specifically, the present invention utilizes acoustics to measure membrane fouling in at least two basic modes; a reflective mode similar to the that described in the references cited in the Background Section, and a total transmission mode as will be described. In the reflective mode, acoustics are used in a reflective manner as generally described in U.S. Pat. No. 6,161,435 along with publications of Chai et. al. and Zhang et. al. However, unlike the cited references wherein acoustic signals are transmitted and received by a transducer mounted to the outer housing of the module, in the present invention the acoustic signals are transmitted from a location adjacent to the permeate collection tube. Echo signals are reflected back from various surface interfaces within the module where they are received at a location preferably adjacent to the permeate collection tube. Interface properties and signal path length change with an increase of fouling on the membrane surface. The change in amplitude, phase and the shift in arrival time of the echo signals compared (via a signal processor) with a reference signal (e.g. corresponding to a non-fouled membrane) so that the relative state of fouling can be measured. As previously described, the location of the transducer near the permeate collection tube allows the measurement of fouling at membrane areas most susceptible to fouling, i.e. near the permeate collection tube. Current testing suggests that reflective mode analysis only provides meaningful data through for a few membrane layers. Most industrial modules include 26 to 30 individual membrane envelopes all wound about the permeate tube. Thus, those areas of membrane most susceptible to fouling are insulated by many layers from the outer housing. Moreover, signal scatter associated with transmission through the module housing is avoided in the present invention. Still further advantages are achieve by locating the transducer within the permeate collection tube. For example, the echo signal corresponding to one or more surfaces of the permeate collection tube provides a convenient reference point for normalizing signals corresponding to membrane surfaces. Such a reference point can be used to eliminate minor variations between transducer; and related set up (e.g. mounting angle) within the tube. Thus, signals corresponding to membrane surfaces are more easily interpreted and more easily compared with reference signals from other modules. Furthermore, echo signals corresponding to one or more surfaces of the permeate collection tube provide a good references point for focusing or initiating signal analysis. That is, the distinctive echo signals corresponding to one or more surfaces of the permeate collection tube provide a cleat reference point for initiating analysis of signals corresponding to membrane surfaces.

In a second embodiment, acoustics are used in a "total transmission mode" which does not rely upon the measurement of time delays of reflective signals. More specifically, acoustic signals are originally transmitted from a location adjacent the permeate collection tube and reflect off an acoustic reference member (see numeral 40 in FIG. 1). The acoustic reference member is typically a strip of metal foil or other surface having a highly differentiate acoustic impedance. The total signal strength (mJ) of the echo signal returning from the acoustic reference member to the transducer is then measured over time. Membrane fouling of membrane surface(s) between the acoustic reference member and transducer absorb, reflect or otherwise diminish the total signal returning to the transducer as a function of time. The total transmission mode of operation is advantageous as it does not require an interpretation of individual echo signals corresponding to many individual interfaces; rather, the measurement simply relies on total received signal strength over a period of time. Increases or decreasing in fouling result in corresponding changes in signal strength over time, the state of membrane fouling can be measured during normal operation or cleaning. Due to the use of total signal strength as a measure of membrane fouling, the acoustic reference member may be separated from the transducer by many membrane envelopes, thus providing collective fouling information on many membrane surfaces.

Whether operating in reflective or total transmission mode, the subject method comprises the steps of:
 a) transmitting an acoustic signal from a location adjacent to the permeate collection tube;
 b) receiving an echo signal resulting from the transmitted acoustic signal reflecting from an interface (e.g. surface of membrane envelope) within the module;
 c) providing a reference signal corresponding to a known state of membrane fouling;
 d) comparing the echo signal to the reference signal; and
 e) determining a state of membrane fouling based upon the comparison of the echo signal and reference signal.

The transmission and receipt of acoustic signals is accomplished by one or more acoustic transducers, as previously described. The steps of transmitting and receiving may be performed in a number of known methods including but not limited to: pulse echo (reflective) mode, and total transmission mode. When operating in the reflective mode with a standard 8 inch commercial RO module, the follow operating parameters are preferred: frequency range from about 0.5 to 20 MHz, preferably 1 to 3 MHz, an energy from about 10 to 200 µJ, preferably 50 to 150 µJ, and a pulse rate of from about 0.1 MHz to 500 KHz. When operating in total transmission mode, the following operating parameters are preferred: frequency range from about 0.01 to 10 MHz, preferably 0.1 to 5 MHz, an energy from about 50 to 2,000 µJ, preferably 100 to 500 µJ, and a pulse rate of from about 0.1 Hz to 500 KHz.

The step of providing a reference signal corresponding to a known state of membrane fouling is most typically accomplished by storing a previously measured signal, such as a signal corresponding to the same module taken at an earlier time during operation (e.g. during normal operation, during the initiation of a cleaning operation, etc,) or a signal value(s) corresponding to a standard reference module, (e.g. a measurement taken from a similar module having a known state of membrane fouling such a substantially clean module). The reference signal may be conveniently stored in a computer memory device or database in order to permit convenient recall. While the phrase "known state of membrane fouling" is intended to refer to a qualitative condition; in some embodiments of the invention, quantitative determinations are also be possible. For example, in one embodiment of the invention, multiple acoustic transducers are located along the length of the permeate collection tube. This use of multiple transducers, i.e. an "array", permits two and/or three dimensional imaging of the membrane surface which can focus on distinct areas of the membrane, or the specific nature of the foulant. Use of arrays of transducers along with corresponding signal processing are well known in the art as described in U.S. Pat. No. 6,305,060 and U.S. Pat. No. 5,460,178, both of which are incorporated herein by reference. Additional background on such acoustic imaging is provided in: *Acoustical Imaging* published by Springer, volumes 1-28, see particularly Volume 27, Arnold, Walter K; Hirsekorn, Sigrun (Eds), Springer (2004), and Volume 28, Andre, Michael P. (Ed), Springer (2007).

It will be appreciated that the sequence of providing a reference signal within the overall method is not critical so long as the reference signal is provided prior to or during the step of comparing the echo signal(s) to the reference signal. For example, the reference signal may be provided prior to or after the steps a) transmitting an acoustic signal, and b) receiving an echo signal.

The step of comparing the echo signal to the reference signal is more generally referred to as "signal processing" and comprises one or more steps of manipulating the signal received from the acoustic transducer(s) by: signal conditioning (e.g. amplification, attenuation, filtering, etc.), signal conversion (e.g. analog-to-digital), signal analysis (e.g. signal transforming via Fourier Transform, evaluation of trends or rates of fouling, use of predictive models) and/or signal storage. These individual operations may be accomplished by a variety of known means and devices which are collectively referred to as a "signal processor". While the transmission and receipt of ultrasonic signals takes place adjacent to the permeate collection tube (preferably within the permeate collection tube), the processing or partial processing of the signals may take place within the permeate collection tube, at a remote location near the spiral wound module and/or at a distantly remote location. In one preferred embodiment, the acoustic transducer(s) are connected to a signal pulser/receiver device by way of a communication means, e.g. a wire, fiber optic conduit, or similar means. The pulser/receiver transmits acoustic signals to the transducer and also receives echo signals from the transducer which may be amplified as is known in the art. The amplified signal may then be communicated to a signal converter, such as an oscilloscope or other known device for converting the analog echo signal into a digital signal. This digital signal may than be further communicated to a computer or similar device for performing a Fourier Transform or similar transformation to the digital signal. The transformation may be accomplished by use of commercially available software suitable for use on a standard personal computer, mainframe computer or similar device. For example, a signal can be transformed into a wavelet for subsequent analysis using commercially available software, e.g. AGU-Vallen Wavelet available from Vallen System GmbH of Munich Germany. Similarly, fast Fourier transform (FFT) software is also commercially available. The resulting "processed signal" may then be stored in a memory device such as in the memory of a standard personal computer, such as in a format of a commercially available software spreadsheet or database. In this format, the processed signal may be easily compared with similarly processed, previously stored, reference signals. The communication means provided between individual unit operations of the signal processor may be via conventional wired connections (e.g. direct copper wire connection, telecommunication lines, internet connections and/or fiber optics), or wireless connections (e.g. a wireless local area network—WLAN) for communicating with the transducers such as a wireless local area network, WiFi, WiMAX, radio, and the like. The subject method may be performed on a continuous, semi-continuous or discontinuous manner.

In a preferred embodiment of the subject method, the step of transmitting an acoustic signal comprises transmitting from a location within the permeate collection tube; and the step of receiving an echo signal comprises receiving at least a portion of the transmitted acoustic signal reflecting from one or more membrane surfaces. As previously mentioned, the echo signal corresponding to one or more surfaces of the permeate collection tube provides a convenient reference point for normalizing signals corresponding to membrane surfaces. Such a reference point can be used to eliminate minor variations between transducers and related set up (e.g. mounting angle) within the tube. Thus, in one preferred embodiment, the subject method comprising the stops of: receiving an echo signal resulting from the transmitted acoustic signal reflecting from one or more surfaces of the permeate collection tube; and normalizing the echo signal reflecting from one or more membrane surfaces with the echo signal reflecting from one or more surfaces of the permeate collection tube. A non-limiting example of this method is provided in the Examples section below.

Figure 5:
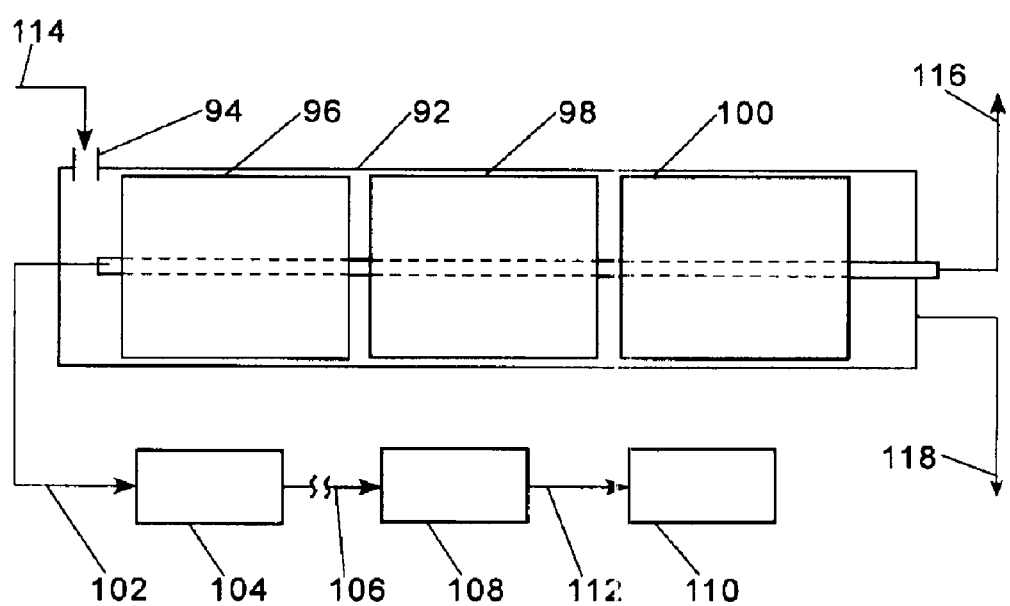
FIG. 5 is a schematic view of a pressure vessel including multiple spiral wound elements connected with a signal processor.
Figure 6:
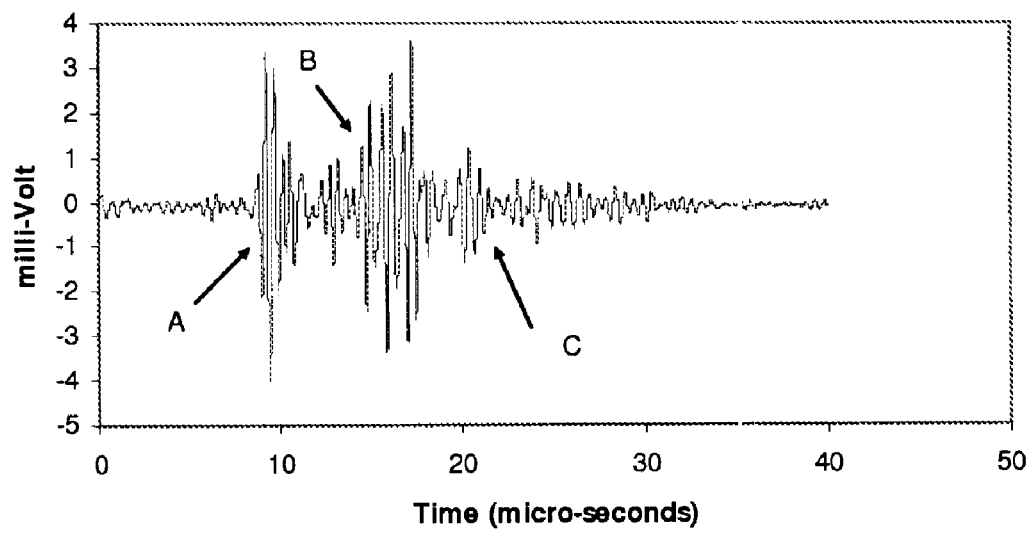
FIG. 6 represents digitized signal read-out representative of a new module with un-fouled membrane operating under the conditions specified in the Examples.
Figure 7:
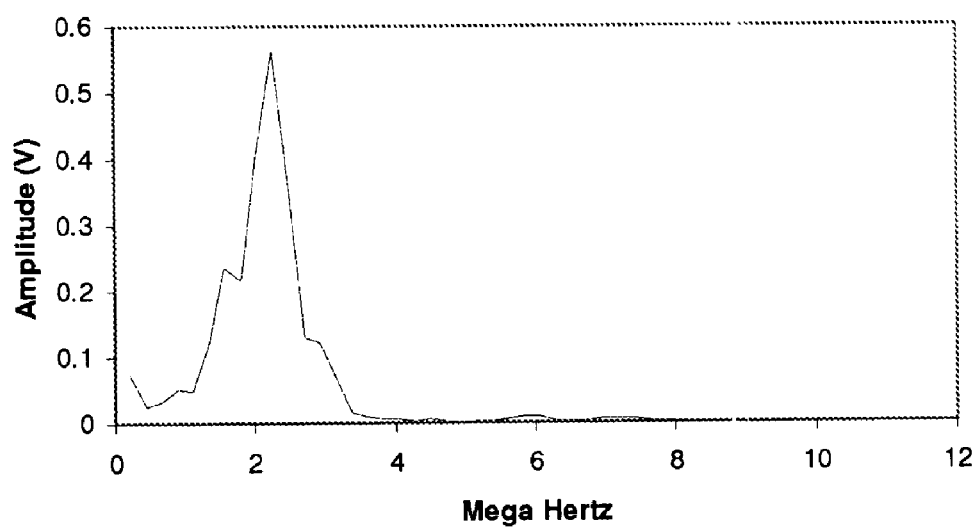
FIG. 7 represents signals of region "A" of FIG. 6 subjected to a Fourier transform and then integrated over a given frequency range.
Figure 8:
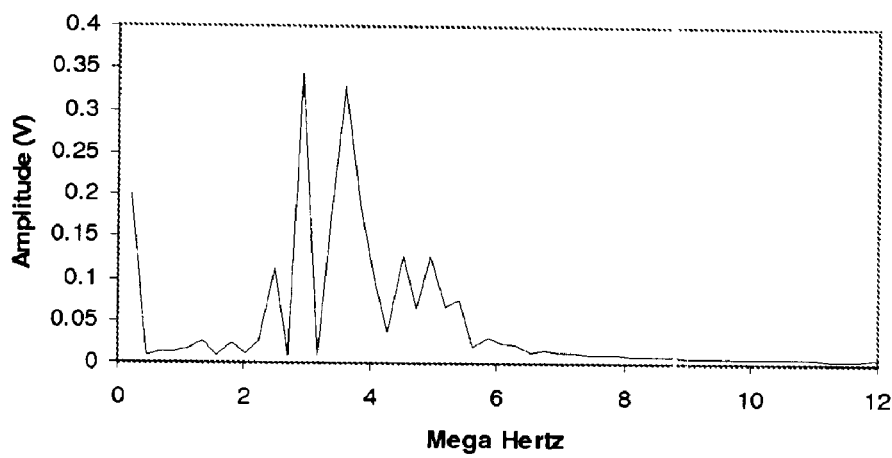
FIG. 8 represents signals of region "C" of FIG. 6 subjected to a Fourier transform and then integrated over a given frequency range.
Figure 9:
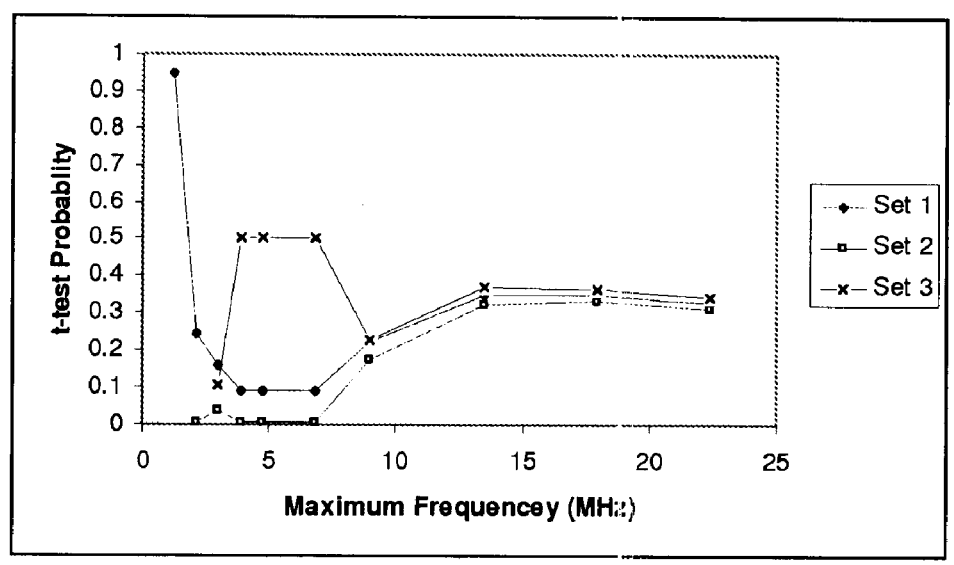
FIG. 9 represents three plots of data from Table 1 compared using a classic t-test.
Figure 10:
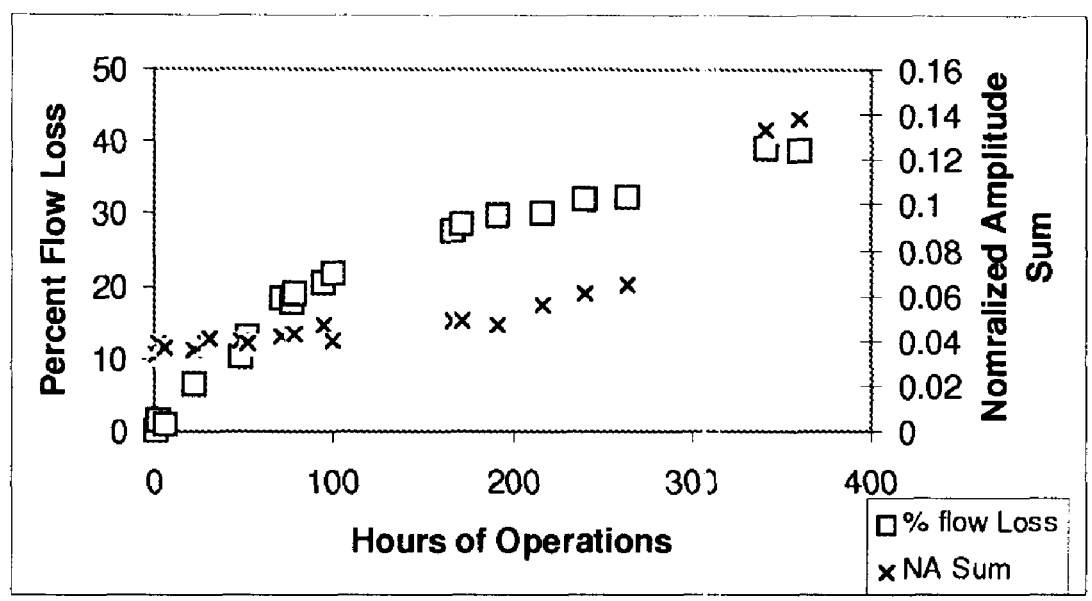
FIG. 10 represents permeate flow measured during an experimental run plotted as a function of time.

One embodiment of the subject invention is illustrated in FIG. 5. In this embodiment, the subject method is preformed as part of continuous or semi-continuous monitoring regime wherein aspects of signal processing are performed at a remote location. With reference to FIG. 5, a pressure vessel (92) is shown including a side feed inlet (94) along with three serial connected spiral wound modules (96, 98, 100). While not shown, one or more transducers are secured within the permeate collection tubes of the modules and are interconnected by a wire (102), as generally shown in FIG. 2 (b). The wire (102) exits the module (96) and pressure vessel (92) and is connected to a signal pulser/receiver (104) located at a position adjacent to the pressure vessel (92), such a control room located on-site with the modules. The signal puller/receiver (104) is connected to a telecommunication or internet line (106) where a conditioned echo signal is transferred to a signal converter (108) located at a remote location. The signal converter (108) converts the analog echo signal to a digital signal which is communicated to a computer (110) via a conventional wire (112) which analyzes the digital signals, e.g. transforms the digital signal by way of a Fourier Transform. The resulting processed signal is then compared with a database reference value stored in the computer. Based upon the comparison of the echo signal to the reference signal, a determination of the state of membrane fouling is made. Once such a determination is made, the operational conditions of the module can be adjusted to optimize system performance, e.g. initiate a cleaning cycle, discontinue a cleaning cycle, adjust pre-treatment conditions, replace the module, etc. This type of embodiment lends itself to remote monitoring and is well suited to spiral wound module assemblies include transducer(s) fixed within the permeate collection tubes such as shown in FIG. 2(b). In operation, feed water (114) enters the pressure housing (92) via the side feed inlet (94). The feed water successively passes through modules (96, 98, 100) with permeate exiting the housing via permeate outlet (116) and concentrate via concentrate outlet (118). Acoustic signals are generated by the pulser/receiver (104) and are communicated to transducers (not shown) located within the modules (96, 98, 100). Echo signals received by the transducers are communicated from the transducers to the pulser/receiver (104) via wire (102). One advantage of monitoring membrane fouling in successive modules is the ability to detect distinct types of fouling. For example, in many industrial applications, silt and biofouling tend to be most pronounced in the first module (96) of a serial arrangement as shown in FIG. 5; whereas scaling ends to be most pronounced in the last module (100) of such a serial arrangement. The use of the subject method to measure different modules within a serial arrangement provides a more comprehensive understanding of both the type and degree of fouling.

In an alternative embodiment, the subject method may be performed as a discontinuous, on-site measurement of membrane fouling utilizing mobile equipment such as a removable probe as described in connection with FIGS. 3 and 4. In such an embodiment, multiple signal processing steps may be performed on-site in an area adjacent to the spiral wound module. For example, a stand-along probe can be connected with a mobile pulser/receiver, oscilloscope and laptop computer to provide on-site signal processing, similar to that previously described.

The step of comparing an echo signal with a reference echo signal may comprise comparing amplitude domain signals, time-domain signals, frequency-domain signals, signal strength-domain signals and combinations thereof, including and/or comparing transformations of such signals.

The step of determining the state of membrane fouling can be made based upon the comparison of the echo signal to the reference signal. In several embodiments, this determination is based upon multiple echo signal comparisons such that both absolute and trend based fouling information can be utilized in making a more accurate determination of the state of membrane fouling. As mentioned, in several embodiments of the invention the determination of membrane fouling is made in real-time during standard operation or during cleaning. Based upon the determination of the state of membrane fouling, the timing and effectiveness of cleaning regimes can be better evaluated. Thus, the length of time between cleaning, cleaning time, and cleaning agents can be optimized. Membrane cleaning regimes are ideally tailored to the specific foulant and the type of membrane. Cleaning methods for spiral wound modules often include flushing with water followed by cleaning chemicals and/or disinfectants. Typically cleaning chemicals include one or more of: alkaline (NaOH) and acid ($HNO_3$, $H_2SO_4$, $H_3PO_4$, etc.). Typical disinfectants include chlorine and hydrogen peroxide. When multiple treatments are used, flushing with clean water between treatment steps is often recommended.

EXAMPLES

An embodiment of the invention was configured in a manner similar to that shown in FIG. 3 including a single FilmTec BW30XLE-440 spiral wound module positioned within a fiberglass pressure vessel. A removable probe was equipped with a Panametrics immersion transducer model A306S-SU including an acoustic reflector as shown in FIG. 3. The transducer was inserted approximately ten inches into the permeate collection tube of the module. The probe was connected to an Olympus pulser/receiver model 5800PR-15-U-9F12. The pulser/receiving settings were as follows: PRF: 100 Hz; Energy: 100 µJ; Damping: 50 ohms; High Filter: 1 MHz; Low Filter 35 MHz; Input Attenuation: 20 dB; Output Attenuation: 9 dB; Gain: 20 dB. The transducer generated a pulse width of one full cycle at 2.225 MHz in water. The pulse width (50% of the maximum amplitude) in frequency space was from 1.45 to 2.69 MHZ. Municipal tap water (Edina Minn.) was used as feed and the system was operated at approximately fifty percent recovery with an in-line pressure of approximately 52-55 pounds per square inch (psi). The pulser/receiver was connected to a Tektronix TDS3024B oscilloscope which converted analog echo signals into a digital format. As will be described, permeate flow measurements and foulant analysis were conducted to validate acoustic signal analysis.

An example of a digitized signal read-out from the oscilloscope is provided in Graph 1. This digital signal is representative of a new module with un-fouled membrane operating under the conditions specified above.

In specific reference to Graph 1, the first set of signals falling between approximately 9 to 11 micro-seconds (designated by region "A") correspond to echo signals from the inner surface of the permeate collection tube. The second set of signals falling between approximately 15 and 18 microseconds (designated by region "B") correspond to echo signals form the outer surface of the permeate collection tube. The signals beyond region B, (designated by region "C") correspond to surfaces within the module concentrically positioned about the permeate collection tube, i.e. membrane surfaces (along with adjacent layers of one or more permeate and spacer sheets).

Region A provides a good measure of the total amount of energy transmitted and received within the system. Consequently, signal losses within the system can be partially normalized by measuring the amplitude of the echo signals within region A and normalizing the remaining measurements to this region. Thus, as described below, echo signals corresponding to the inner surface of the permeate collection tube provide a convenient reference point for determining signal loss within the system. Additionally, it can be helpful to eliminate signals that provide little or no information regarding the membrane surface. Utilizing the distinctive echo signals corresponding to the inner and outer surfaces (regions A and B) of the permeate collection tube also provides a good reference point for signal analysis.

In order to provide a basis for signal normalization, the signals of region "A" were subjected to a Fourier transformed and the frequency dependent amplitude was then integrated over a given frequency range, the results of which are presented in Graph 2. This same procedure was repeated for region "C" and is presented in Graph 3.

Signal analysis was investigated by initiating flow of feed through the module and taking nine consecutive signal measurements during the course of the experimental run. The first four signal measurements were taken prior to any substantive fouling, i.e. "non-fouled state". This non-fouled data set was compared with the five subsequent signal measurements taken when the average flow of the module had been reduced by an average of eight percent, i.e. "fouled state". These two data sets, "non-fouled vs. fouled" were normalized and then compared using a classic t-test. More specifically, the data sets were normalized by subjecting the individual signal measurements to Fourier transform to determine amplitudes at different frequencies. The amplitudes of different frequencies corresponding to the signals of region C were summed and divided by the same sum of the reference signals from region A, to generate a "normalized amplitude sum". In this way, the signals of region C could be normalized to take into account the variations within the system. As there was a significant contribution at the zero frequency (see Graphs 2 and 3), a clear off-set was identified. As shown in Table 1, a first set of normalized amplitude sums is labeled "First set" and includes the sum of frequencies from 0 through 22.36 Mega Hertz. A second and third set are also provided but with off-sets of 0.11 and 1.22 Mega Hertz, respectively.

TABLE 1

| First Set | | Second Set | | Third Set | |
|---|---|---|---|---|---|
| Start: | Final: | Start: | Final | Start | Final |
| Min. Freq. (MHz) | Max. Freq. (MHz) | Min. Freq. (MHz) | Max. Freq. (MHz) | Min. Freq. (MHz) | Max. Freq. (MHz) |
| 0 | 0.33 | 0.11 | 0.33 | 1.22 | — |
| 0 | 1.22 | 0.11 | 1.22 | 1.22 | — |
| 0 | 2.11 | 0.11 | 2.11 | 1.22 | 2.11 |
| 0 | 3.00 | 0.11 | 3.00 | 1.22 | 3.00 |
| 0 | 3.89 | 0.11 | 3.89 | 1.22 | 3.89 |
| 0 | 4.78 | 0.11 | 4.78 | 1.22 | 4.78 |
| 0 | 6.79 | 0.11 | 6.79 | 1.22 | 6.79 |
| 0 | 9.01 | 0.11 | 9.01 | 1.22 | 9.01 |
| 0 | 13.46 | 0.11 | 13.46 | 1.22 | 13.46 |
| 0 | 17.91 | 0.11 | 17.91 | 1.22 | 17.91 |
| 0 | 22.36 | 0.11 | 22.36 | 1.22 | 22.36 |

Three plots of data from Table 1 were compared using a classic t-test, the results of which are illustrated in Graph 4. As shown in Graph 4, use of the normalized amplitude sums without a contribution from the zero frequency increased the probability of finding a difference between the data sets (non-fouled vs. fouled) from ninety percent (90%) to less than ninety-nine (99%).

Permeate flow was measured during an experimental run and is plotted as a function of time below in Graph 5. Graph 5 additionally includes a plot of a subset of the Second Set of data (normalized amplitude sums) from Table 1 with a starting minimum frequency of 0.11 MHz and a final maximum frequency of 3.00. MHz.

During one experimental run, feed flow was discontinued once permeate flow diminished by approximately ten percent. The module was then cleaned with a solution of citric acid. After cleaning, permeate flow was fully recovered to its original un-fouled state. The resulting cleaning solution was subjected to elemental analysis, portions of which are summarized in Table 2. Based upon the membrane surface area within the module and the iron and calcium recovered from the cleaning solution, it was determined that approximately one half of one gram of these two "foulants" were present per square foot of membrane.

TABLE 2

Water analysis for selected elements: feed water, permeate, concentrate - before and after cleaning with 1% citric acid.

| Source | Selected Element (mg/l) | | | | | | | | |
|---|---|---|---|---|---|---|---|---|---|
| | Ba | Ca | Cu | Fe | Mg | Mn | P | K | Na |
| Feed | 0.137 | 83.10 | 0.180 | 0.123 | 34.25 | 0.014 | 0.421 | 1.542 | 8.76 |
| Permeate | 0.001 | 0.679 | <0.005 | <0.005 | 0.278 | <0.001 | <0.098 | 0.150 | 0.919 |
| Concentrate | 0.230 | 142.5 | 0.327 | 0.124 | 58.12 | 0.023 | 0.522 | 2.885 | 16.4 |
| Before Cleaning | 0.165 | 84.33 | 0.615 | 1.390 | 33.94 | 0.085 | 0.640 | 1.295 | 10.29 |
| After Cleaning | 3.150 | 245.8 | 16.82 | 98.10 | 41.39 | 5.660 | 16.06 | 1.360 | 10.64 |

Thus, as demonstrated by the examples, acoustic signals measurements can be correlated with loss of permeate flow and elemental analysis of membrane foulants.

While much of the detailed description of spiral wound modules has focused upon traditional RO and NF applications, those skilled in the art will readily appreciate the applicability to other spiral wound modules including but not limited to those directed toward UF, MF, electro-dialysis, electro deionization along with modules designed for gas separation and non-aqueous liquid feeds. While principles of the invention are amenable to various modifications and alternatives forms, particular species have been described by way of examples, drawings and detailed description. It should be understood that the intent of this description is not to limit the invention to the particular embodiments described, but rather to cover all modifications, equivalents, and alternatives falling within the spirit and scope of the disclosure.

The invention claimed is:

1. A method of measuring membrane fouling within a spiral wound module wherein the module comprises a permeate collection tube, at least one membrane envelope wound about the permeate collection tube, and an outer housing; said method comprising the steps of:
   a) transmitting an acoustic signal from within the permeate collection tube;
   b) receiving an echo signal resulting from the transmitted acoustic signal reflecting from an interface within the module;
   c) providing a reference signal corresponding to a known state of membrane fouling;
   d) comparing the echo signal to the reference signal; and
   e) determining a state of membrane fouling based upon the comparison of the echo signal and reference signal.

2. The method of claim 1 wherein the steps of transmission and reception of acoustic signals are performed by at least one acoustic transducer located within the permeate collection tube.

3. The method of claim 1 wherein the step of comparing the echo signal to a reference signal comprising comparing the echo signal to at least one of:
   a) a signal corresponding to a known state of membrane fouling; and
   b) a signal of the subject module measured at an earlier time.

4. The method of claim 1 wherein the echo signal comprises at least a portion of the transmitted acoustic signal reflecting from an acoustic reference member located between the permeate collection tube and the outer housing; and wherein the step of comparing the echo signal to a reference signal comprises comparing the signal strength-time domain.

5. The method of claim 1 wherein the step of comparing the echo signal to the reference signal further comprises the steps of amplifying the echo signal, converting the echo signal from analog to digital, and transforming the digital signal.

6. The method of claim 1 wherein the step of comparing the echo signal to the reference signal and the step of determining a state of membrane fouling are performed at a location remote from the spiral wound module.

7. The method of claim 1 wherein:
   the step of transmitting an acoustic signal comprises transmitting from a location within the permeate collection tube;
   the step of receiving an echo signal comprises receiving at least a portion of the transmitted acoustic signal reflecting from one or more membrane surfaces and from one or more surfaces of the permeate collection tube; and
   normalizing the echo signal reflecting from one or more membrane surfaces with the echo signal reflecting from one or more surfaces of the permeate collection tube.

\* \* \* \* \*